United States Patent [19]

Reinhoudt et al.

[11] Patent Number: 5,380,423
[45] Date of Patent: Jan. 10, 1995

[54] ANION-SELECTIVE MEMBRANE AND A SENSOR PROVIDED THEREWITH

[75] Inventors: David N. Reinhoudt, Hengelo; Johannes F. J. Engbersen, Ede; Willem Verboom, Vriezenveen; Dimitri Rudkevich; Walter P. R. V. Stauthamer, both of Enschede, all of Netherlands

[73] Assignee: Priva Agro Holding B.V., Netherlands

[21] Appl. No.: 136,675

[22] Filed: Oct. 15, 1993

[30] Foreign Application Priority Data

Oct. 15, 1992 [NL] Netherlands ............... 9201794

[51] Int. Cl.$^6$ ............................................. G01N 27/26
[52] U.S. Cl. ..................................... 204/418; 204/296
[58] Field of Search ................ 204/418, 296; 521/27

[56] References Cited

U.S. PATENT DOCUMENTS 4,784,736  11/1988  Lonsdale et al. ............... 204/157.15
5,238,548   8/1993  van der Wal et al. ............. 204/418

FOREIGN PATENT DOCUMENTS 0177544  10/1985  European Pat. Off. .
0258951  12/1993  European Pat. Off. .
63-005256 11/1988  Japan .
8400916  10/1985  Netherlands .
8602242   4/1988  Netherlands .
9100184   9/1992  Netherlands .
9100872  12/1992  Netherlands .

OTHER PUBLICATIONS

Chem Abstracts, van Staaten–Nijenhuis, 1994*, CA120(2):16064f.
A. R. van Doorn et al., "Molecular Recognition of Neutral Molecules by Metalloclefts: Synthesis, X-ray Structure, H NMR Spectroscopy, Electrochemistry, and Molecular Modeling", *Journal of Organic Chemistry*, vol. 56, 1991, pp. 2371–2380.
C. J. van Staveren et al., "Cocomplexation of Neutral Guests and Electrophilic Metal Cations in Synthetic Macrocylic Hosts", *Journal of the American Chemical Society*, vol. 110, 1988, no month presently available pp. 4994–5008.

*Primary Examiner*—John Niebling
*Assistant Examiner*—Bruce F. Beu
*Attorney, Agent, or Firm*—Webb Ziesenheim Bruening Logsdon Orkin & Hanson

[57] ABSTRACT

The invention relates to a membrane that is selective for anions, particularly phosphate, comprising an ionophore based on a uranyl complex with the annexed general formula, wherein A, B, C, D=R
A+B+C+D=($C_5$–$C_7$) aryl, ($C_5$–$C_7$) cycloalkyl, ($C_1$–$C_{30}$) alkyl ($C_5$–$C_{10}$) aryl, ($C_1$–$C_{30}$) alkyl ($C_5$–$C_{10}$) cycloalkyl, E+E′, G+G′=aryl, such as phenyl and naphthyl, or aryl substituted with a substituent ($C_1$–$C_{30}$) alkoxy, or aryl substituted with the individual substituent or the substituent joined by ring closure K and/or K—CONH—L, wherein K, L=H —R—$(CH_2)_m$—, —R—$(CH_2)_m$—R, —X—$(CH_2)_m$—, —X$(CH_2)_m$—R, —X—$(CH_2)_m$—X, —X$(CH_2)_m$—X—R, —RX$(CH_2)_m$—, —RX$(CH_2)_m$—XR, —X—(R—X)$_n$—, wherein X=O, S; m=0–10 and n=0–10
R=($C_1$–$C_{30}$) alkyl, ($C_5$–$C_{10}$) aryl, ($C_5$–$C_{10}$) cycloalkyl, ($C_1$–$C_{30}$) alkyl ($C_5$–$C_{10}$) aryl, ($C_1$–$C_{30}$) alkyl ($C_5$–$C_{10}$) cycloalkyl, wherein alkyl is a straight or branched chain and wherein aryl and alkyl are optionally substituted with ($C_1$–$C_{30}$) alkyl halogen nitro cyano hydroxy.

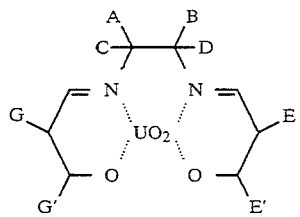

17 Claims, No Drawings

ANION-SELECTIVE MEMBRANE AND A SENSOR PROVIDED THEREWITH

The present invention relates to an anion-selective membrane, in particular a membrane that is selective for the phosphate ion, particularly dihydrogen phosphate. The present invention further relates to a sensor in which such an anion-selective membrane is included. Such sensors are used for measuring the concentration of the anion in an electrolyte solution such as fertilizer dosages in the market gardening sector. Examples of suitable sensors are the ISFET, ion-selective electrode, optrode, coated-wire electrode and sensors on the basis of planar silicon technology.

The membrane is anion-selective due to a specific ionophore for the anion present therein. The ionophore can be physically and/or chemically (covalently) bonded to the membrane matrix. Examples of such physical and chemical methods of bonding are described in NL-A-8400916 NL-A-8602242, NL-A-9100184 and NL-A-9100872.

The present invention is based on the discovery that specific ionophores based on a uranyl complex exhibit a very high thermodynamic stability in combination with a high selectivity for anions, particularly for dihydrogen phosphate. The ionophore is moreover neutral, which is favourable for applications in electrolyte solutions.

In its widest aspect the present invention relates to a membrane that is selective for anions, particularly phosphate, comprising an ionophore based on a uranyl complex with the general formula

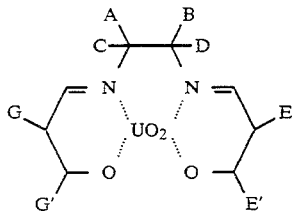

wherein
A, B, C, D = R
A+B+C+D = $(C_5-C_7)$ aryl, $(C_5-C_7)$ cycloalkyl, $(C_1-C_{30})$ alkyl $(C_5-C_{10})$ aryl, $(C_1-C_{30})$ alkyl $(C_5-C_{10})$ cycloalkyl
E+E', G+G' = aryl, such as phenyl and naphthyl, or aryl substituted with a substituent $(C_1-C_{30})$ alkoxy, or aryl substituted with the individual substituent or the substituent joined by ring closure
K and/or
K—CONH—L, wherein
K, L = H —R—$(CH_2)_m$—, —R—$(CH_2)_m$—R, —X—$(CH_2)_m$—, —X$(CH_2)_m$—R, —X—$(CH_2)_m$—X, —X$(CH_2)_m$—X—R, —RX$(CH_2)_m$—, —RX$(CH_2)_m$—XR, —X—(R—X)$_n$—, wherein
X = O, S
m = 0–10 and
n = 0–10
R = $(C_1-C_{30})$ alkyl, $(C_5-C_{10})$ aryl, $(C_5-C_{10})$ cycloalkyl, $(C_1-C_{30})$ alkyl $(C_5-C_{10})$ aryl, $(C_1-C_{30})$ alkyl $(C_5-C_{10})$ cycloalkyl
wherein alkyl is a straight or branched chain optionally substituted with
$(C_1-C_{30})$ alkyl halogen nitro cyano hydroxy;
wherein aryl is optionally substituted with $(C_1-C_{30})$ alkyl halogen nitro cyano hydroxy.

In preference the ionophore contains a —CONH group whereby the stability and usually the selectivity for dihydrogen phosphate further increases. For this purpose it is recommended that the substituent E+E' and/or the substituent G+G' is aryl substituted with the group K—CONH—L. The synthesis of such ionophores is furthered when more preferably the group K—CONH—L is the group X—$(CH_2)_m$—CONH—L.

If in this case the substituent L is further an alkyl, aryl, cycloalkyl, alkylaryl or alkylcycloalkyl group, the stability and selectivity for dihydrogen phosphate is then increased further. Moreover achieved herein is that leaching of ionophore physically bonded in the membrane is further suppressed, particularly in the case of alkyl groups in which the number of carbon atoms amounts to 6 or more, such as $C_{16}-C_{30}$, particularly $C_{16}$ and $C_{18}$. Optimal stability and selectivity are obtained when the substituent L is an aryl group which can optionally be substituted.

Very favourable ionophores for use in the present invention are those in which the substituent is a joint substituent K—COHN—L—NHCO—K formed by ring closure. From the point of view of synthesis it is further recommended that the group L is $(CH_2)_m$—X—$(CH_2)_m$—X—$(CH_2)_m$, wherein preferably m = 2 and X = O. Thus created is an ionophore with a very high stability and selectivity for dihydrogen phosphate.

In another group of ionophores for use in a membrane according to the invention it is recommended that the substituent E+E' and/or the substituent G+G' is aryl substituted with —X—$(CH_2)_m$H. Such ionophores have the highest selectivity for dihydrogen phosphate. In preference X = O.

The ionophore can be further provided with a large diversity of reactive groups for chemical covalent bonding of the ionophore to the membrane matrix. This linking group can be included in all substituents A, B, C, D, E, E', G and G'. In preference the linking group is included in an aryl group.

Suitable linking groups are

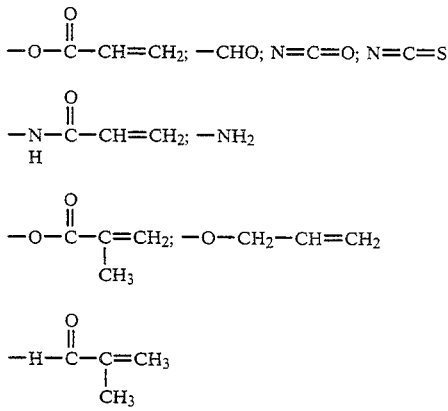

This chemical linking can take place through the reaction of the linking group with a functional group in the matrix, or by polymerization during the forming of the matrix.

For exclusive or supplementary physical linking of the ionophore in the membrane matrix it is further recommended that the ionophore be provided with a linking group with a high lipophilicity such as for instance alkyl, alkylaryl, alkylcycloalkyl groups with 5 and more carbon atoms, in general 5 to 30 carbon atoms, such as $C_{12}$–$C_{24}$, particularly $C_{16}$ and $C_{18}$.

Preferred ionophores at this time are the ionophores with the following structure formulae:

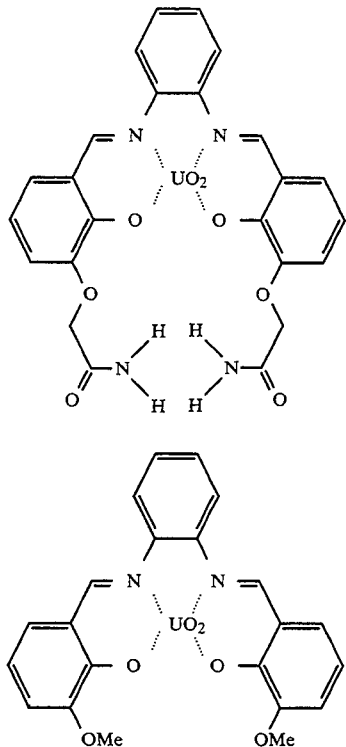

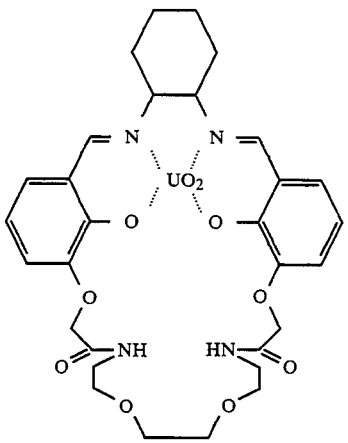

Of a number of ionophores according to the invention for selective measurement of anions, particularly dihydrogen phosphate, the association constants for a number of anions were measured such as chloride, dihydrogen phosphate, hydrogen sulphate, nitrite and thiocyanate. Use is made herein of a solution of 1% dimethylsulphoxide in acetonitrile. The measurements were performed by diluting a sample solution with a stock solution of the free salt. The sample solution was prepared by adding small quantities of free ligand to 10 ml stock solution. The starting concentrations were 1–2 mM for the ligand and 0.3–0.7 mM for the salt. The $K_{ass}$ values were determined conductometrically using curve-fitting methods. The results are shown in the following table.

| ionophore | 1 | 2 | 3 | 4 | 5 | 6 |
|---|---|---|---|---|---|---|
| anion | a | a | a | a | a | a |
| $Cl^-$ | $4,0 \times 10^2$ | $9,5 \times 10^2$ | $8,7 \times 10^2$ | $5,1 \times 10^3$ | $6,8 \times 10^1$ | $7,1 \times 10^3$ |
| $H_2PO_4^-$ | $1,5 \times 10^4$ | nd | nd | $1,9 \times 10^4$ | $2,0 \times 10^4$ | $1,9 \times 10^4$ |
| $HSO_4^-$ | $4,5 \times 10^1$ | nd | nd | $4,8 \times 10^1$ | $2,8 \times 10^1$ | nd |
| $NO_2^-$ | $3,1 \times 10^2$ | $7,4 \times 10^2$ | $7,5 \times 10^2$ | $2,1 \times 10^3$ | $6,7 \times 10^1$ | nd |
| $SCN^-$ | $5,0 \times 10^1$ | $7,1 \times 10^1$ | $8,2 \times 10^1$ | $1,7 \times 10^2$ | $1,4 \times 10^1$ | nd |
| ionophore | 7 | 8 | 9 | 10 | 11 | 12 |
| anion | a | a | a | a | a | a |
| $Cl^-$ | $4,0 \times 10^3$ | $1,7 \times 10^3$ | $2,2 \times 10^{2\ 2)}$ | $1,2 \times 10^4$ | $2,5 \times 10^2$ | nb |
| $H_2PO_4^-$ | $1,9 \times 10^4$ | $2,5 \times 10^6$ | $1,6 \times 10^3$ | $>5 \times 10^6$ | nd | $1,1 \times 10^5$ |
| $HSO_4^-$ | nd | $1,4 \times 10^2$ | nd | nd | nd | nd |
| $NO_2^-$ | $8,9 \times 10^2$ | $4,5 \times 10^2$ | $1,2 \times 10^{2\ 2)}$ | nd | nd | nd |
| $SCN^-$ | nd | $7,1 \times 10^1$ | $1,8 \times 10^{1\ 2)}$ | nd | nd | nd |

[1)] nd means not determined
[2)] solvent acetonitrile

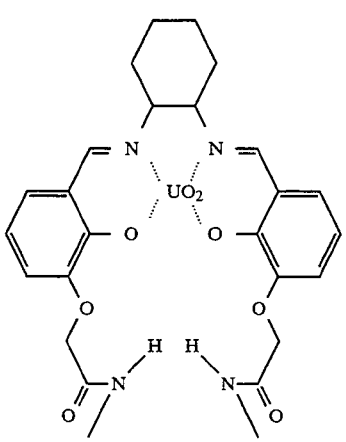

Example 1

Preparation of ionophore 6

A mixture of bromoacetamide (10 mM) (3-hydroxy-2-(2-propenoxy)benzaldehyde (from C. J. van Staveren et al, Journal American Chemicals Recited, 1988, 110, page 4994) (10 mM) and $K_2CO_3$ (20 mM) in $CH_3CN$ (200 ml) was refluxed for 10–12 hours. The solution was filtered whereby the solvent was evaporated. The remaining solid was purified by recrystallization from 2-propanol. The yield amounted to 87%, melting point 128° C.

$^1$H NMR data: δ10.40 (s, CHO), 7.2–7.6 (m, 3H, Ar H), 6.85 (br s, 1H, NH), 6.0–6.2 (m, 1H, OCH$_2$CHCH$_2$), 6.0 (br s, 1H, NH), 5.3–5.5 (m, 2H, OCH$_2$CHCH$_2$), 4.66 (d, 2H, OCH$_2$CHCH$_2$), 4.58 (s, 2H, CH$_2$CO). IR (KBr) data: 1684 (CHO) cm$^{-1}$. Mass Spectrum (EI): m/z 235.0 (calculated 235.1). Element analysis for C$_{12}$H$_{13}$NO$_4$: calculated C=61.28; H=5.53; N=5.96. Found: C=61.13; H=5.55; N=5.96.

The prepared allyl compound (3 mM), Pd(OAc)$_2$ (0.1 mM), PPh$_3$, (0.5 mM), NEt$_3$ (37 mM) and HCOOH (37 mM) in 80% aqueous ethanol (60 ml) was refluxed for 45 minutes. Ethanol was evaporated and the total water volume was adjusted to 100 ml. The mixture was extracted with CH$_2$Cl$_2$. The organic layer was dried over Na$_2$SO$_4$, concentrated under vacuum and purified by flash chromatography (SiO$_2$; acetone). The yield amounted to 55%, melting point 132°–133 ° C.

$^1$NMR data: δ10.18 (s, CHO), 7.46 (d, J=8.0 Hz, 1H ArH), 7.34 (d, J=8.0 Hz, 1H, ArH), 7.30 (br s, 1H, NG), 7.00 (t, J=9.0 Hz, 1H ArH), 6.92 (br s, 1H NH), 4.55 (s, 2H, CH$_2$CO). IR (KBr) data: 1696 (CO), 1652 (CHO) cm$^{-1}$. Mass spectrum (EI): m/z 195.0 (calculated 195.1). Element analysis for C$_9$H$_9$NO$_4$H$_2$O: calculated C=51.92; H=4.29; N=6.73. Found: C=52.23; H=4.47; N=6.63. Karl Fischer titration: calculated for 1H$_2$O=8.45, found: 8.66.

The solution of the aldehyde (10 mM) and 1,2-benzenediamine (5 mM) in methanol (100 ml) was refluxed for 1 hour. A solution of UO$_2$(OAc)$_2$H$_2$O (5 mM) in methanol (10 ml) was then added and the reaction mixture refluxed for 1 hour. A formed precipitation was filtered and washed with methanol. Yield 71%, melting point >265° C.

$^1$H NMR data: δ9.52 (s, 2H, HC=N), 7.87 (s, 2H, NH), 7.70 (m, 2H, ArH), 7.56 (s, 2H, NH), 7.50 (m, 2H ArH), 7.42 (d, J=8.0 Hz, 2H, ArH), 7.35 (d, J=8.0 Hz, 2H, ArH), 6.67 (t, J=8.0 Hz, 2H, ArH), 4.70 (s, 4H, CH$_2$CO). IR (KBr) data: 1663 (CO), 1604 (C=N), 900 (O-U-O) cm$^{-1}$. Mass spectrum (FAB): m/z 731.2 (calculated 731.2). Element analysis: calculated for C$_{24}$H$_{20}$N$_4$O$_8$U 1.8 H$_2$O; calculated C=37.76; H=3.10; N=7.34. Found: C=37.10; H=2.70; N=6.54. Karl Fischer titration: calculated for 1.8 H$_2$O: 4.25. Found: 4.29.

Example 2

Ionophore 7

The same preparation method was followed as for ionophore 6, wherein cis-1,2-cyclohexane was used instead of 1,2-benzenediamine.

The yield amounted to 77%, melting point >265° C.

$^1$H NMR data: δ9.32 (s, 2H, HC=N), 8.05 (br s, 2H, NH), 7.46 (br s, 2H, NH), 7.30 (two d, J=8.0 Hz, 4H, ArH), 6.61 (t, J=8.0 Hz, 2H, ArH), 4.67 (s, 4H, CH$_2$CO), 4.60 (m, 2H, CH-cycl), 2.40 (m, 2H, CH-cycl), 1.7–2.0 (m, 6H, CH-cycl). IR (KBr) data: 1666 (CO), 1615 (C=N), 900 (O-U-O) cm$^{-1}$. Mass spectrum (FAB): m/z 737.5 (calculated 737.2). Element analysis: calculated for C$_{24}$H$_{26}$N$_4$O$_8$U 1.9 H$_2$O: C=37.39; H=3.87; N=7.27. Found: C=36.86; H=3.50; N=7.03. Karl Fischer titration: calculated for 1.9 H$_2$O: 4.43. Found: 4.41.

Example 3

Ionophore 8

A mixture of N-p-tolylbromoacetamide (10 mM), benzaldehyde (10 mM) and K$_2$CO$_3$ (20 mM) in CH$_3$CN (200 ml) was refluxed for 10–12 hours. The solution was filtered and the solvent was evaporated. The remaining solid was purified by recrystallization from 2-propanol. Yield 76%, melting point 98 ° C.

$^1$H NMR data: δ10.46 (s, 1H, CHO), 8.60 (s, 1H, NH), 7.2–7.6 (m, 3H, ArH), 7.45 (d, J=8.0 Hz, 2H, ArH), 7.18 (d, J=8.0 Hz, 2H, ArH), 6.15 (m, 1H, OCH$_2$CHCH$_2$), 4.66 (s, 2H, CH$_2$CO), 2.32 (s, 3H, CH$_3$). Mass spectrum (EI): m/z 325.0 (calculated 325.1). Element analysis: calculated for C$_{19}$H$_{19}$NO$_4$: C=70.15; H=5.85; N=4.31. Found: C=69.48; H=5.93; N=4.15.

The formed allyl compound (3 mM), Pd(OAc)$_2$ (0.1 mM), PPh$_3$, (0.5 mM), NEt$_3$ (37 mM) and HCOOH (37 mM) in 80% aqueous ethanol (60 ml) was refluxed for 1 hour. Ethanol was evaporated and the total water volume was adjusted to 100 ml. The mixture was extracted with CH$_2$Cl$_2$. The organic layer was dried over Na$_2$SO$_4$, concentrated under vacuum and purified by flash chromatography (SiO$_2$; acetone). The yield amounted to 53%, melting point 84°–85° C.

$^1$H NMR data: δ11.35 (s, 1H, OH), 9.91 (s, 1H, CHO), 8.87 (s 1H, NH), 7.53 (d, J=8.0 Hz, 2H, ArH), 7.31 (d, J=7.7 Hz, 1H, ArH), 7.20 (d, J=7.7 Hz, 1H, ArH), 7.12 (d, J=8.0 Hz, 2H, ArH), 7.00 (t, J=7.7 Hz, 1H, ArH), 4.67 (s, 2H, CH$_2$CO), 2.31 (s, 3H, CH$_3$). IR (KBr) data: 1688 (CO), 1665 (CHO). Mass spectrum (EI): m/z 285.1 (calculated 285.1) Element analysis: calculated for C$_{16}$H$_{15}$NO$_4$ 0.56 H$_2$O: C=65.04; H=5.10; N=4.74. Found: C=64.62; H=5.41; N=4.55. Karl Fischer titration: calculated for 0.56 H$_2$O: 3.43. Found: 3.44.

The solution of the formed aldehyde (10 mM) and 1,2-cis-cyclohexanediamine (5 mM) in methanol (100 ml) was refluxed for 1 hour. A solution of UO$_2$(OAc)$_2$2H$_2$O (5 mM) in methanol (10 ml) was then added and the reaction mixture refluxed for 1 hour. The reaction mixture was cooled to room temperature. The formed precipitation was filtered and washed with methanol. Yield amounted to 79% melting point 249°–251° C. (decomposition).

$^1$H NMR data: δ10.55 (s, 2H, NH), 9.50 (s, 2H, CH=N), 7.60 (d, J=8.0 Hz, 4H, ArH), 7.45–7.55 (two d, J=8.0 Hz, 4H, ArH), 6.95 (d, J=8.0 Hz, 4H, ArH), 6.73 (t, J=8.0 Hz, 2H, ArH), 5.02 (s, 4H, CH$_2$CO), 4.65 (m, 2H, CH-cycl), 2.45 (m, 2H, CH-cycl), 2.33 (s, 6H, CH]), 1.7–2.0 (m, 6H, CH-cycl). IR (KBr) data: 1685 (CO), 1617 (C=N), 904 (O-U-O). Mass spectrum (FAB): m/z 917.8 (calculated 917.3). Element analysis: calculated for C$_{38}$H$_{38}$N$_4$O$_8$U 1.75 H$_2$O: C=48.11; H=4.04; N=5.91. Found: C=47.22; H=4.17; N=5.72. Karl Fischer titration: calculated for 1.75 H$_2$O: 3.32. Found: 3.35.

It was possible to prepare another ionophore in the same manner as for ionophore 8, wherein 1,2-benzenediamine was used instead of 1,2-cis-cyclohexanediamine. The yield amounted to 64%, melting point 260° C. (decomposition).

$^1$H NMR data: δ10.69 (s, 2H, NH), 9.28 (s, 2H, CH=N), 7.58 (d, J=8.0 Hz, 4H, ArH), 7.3–7.5 (m, 4H, ArH), 7.25 (two d, J=8.0 Hz, 4H, ArH), 7.15 (t, J=8.0 Hz, 2H, ArH), 6.65 (d, J=8.0 Hz, 4H, ArH), 5.00 (s, 4H, CH$_2$CO), 2.33 (s, 6H, CH$_3$). IR (KBr) data: 1667 (CO), 1604 (C=N), 906 (O-U-O). Mass spectrum (FAB): m/z 911.8 (calculated 911.3). Element analysis: calculated for $C_{38}H_{32}N_4O_8U$ 1.52 $H_2O$: C=48,65; H=3,74; N=5,97, Found: C=48.17; H=3,57; N=5.71. Karl Fischer titration: calculated for 1.52 H20: 2.91. Found: 2.91.

Example 4

Ionophore 9

A solution of the methylmethylether of 2,2'-dihydroxy-[1,1'-biphenyl] (10 mM) in tetrahydrofuran (50 ml) was mixed with tertiary butyl lithium (22 mM in 1.5M solution in pentane) per 10° C. After stirring for 2 hours dimethylformamide (25 mM) was added and the reaction mixture was stirred for 1 hour at room temperature. The mixture was quenched with a saturated watery solution of $NH_4Cl$ and was extracted with $CH_2Cl_2$. The organic layer was washed with water, dried over $Na_2SO_4$ and concentrated under vacuum. The product was purified by flash chromatography ($SiO_2$; $CH_2Cl_2$). The yield amounted to 63%.

$^1$H NMR data: δ10.41 (s, 1H, CHO), 7.90 (d, J=8.0 Hz, 1H ArH), 7.61 (d, J=8.0 Hz, 1H, ArH), 6.95–7.45 (m, 5H, ArH), 6.27 (br s, 1H, OH), 4.80 (s, 2H, $CH_2$), 3.29 (s, 3H, $CH_3$). IR (KBr) data: 1684 (CHO). Mass spectrum (EI): m/z 285.0 (calculated 285.0). Element analysis: calculated for $C_{15}H_{14}O_4$: C=69.77; H=5.43. Found: C=69.81; H=5.94.

A mixture of the formed aldehyde (10 mM) (bromoacetamide) (10 mM) and $K_2CO_3$ (20 mM) in $CH_3CN$ (200 ml) was refluxed for 10–12 hours. The solution was filtered and the solvent was evaporated. The remaining oil was quenched with methanol containing hydrochloric acid (prepared in situ from NaCl and concentrated $H_2SO_4$) and stirred for 15–20 minutes to remove the ortho-positioned methylmethylether. Water was then added and the pH was adjusted to 7 with 0.1M NaOH, and the obtained mixture was extracted with $CH_2Cl_2$. The organic layer was washed with $H_2O$, dried over $Na_2SO_4$ and concentrated under vacuum. The product was purified by flash chromatography ($SiO_2$; $CH_2Cl_2$-acetone. 10:1). The yield amounted to 54%, melting point 114°–116 ° C.

$^1$H NMR data: δ11.56 (s, 1H, OH), 9.95 (s, 1H, CHO) 7.61 (d, J=7.9 Hz, 1H, ArH), 7.54 (d, J=7.9 Hz, 1H, ArH), 7.41 (d, J=7.9 Hz, 1H, ArH), 7.39 (t, J=7.9 Hz, 1H, ArH), 7.2–7.7 (m, 2H, ArH), 7.00 (d, J=7.9 Hz, 1H, ArH), 6.90 (br s, 1H, NH), 6.35 (br s, 1H NH), 4.50 (s, 2H, $CH_2CO$. IR (KBr) data:. 1693 (CO), 1661 (CHO). Mass spectrum (EI): m/z 271.1 (calculated 271.1).

A solution of the formed aldehyde (10 mM) and 1,2-cis-cyclohexanediamine (5 mM) in methanol (100 ml) was refluxed for 1 hour. A solution of $UO_2(OAc)_2 2H_2O$ (5 mM) in methanol (10 ml) was then added and the reaction mixture refluxed for 1 hour. The reaction mixture was cooled to room temperature. The precipitation was evaporated partially dry, filtered and washed with methanol. The yield amounted to 71%, melting point 243° C. (decomposition).

$^1$H NMR data: δ9.51 (s, 2H, CH=N), 7.65 (d, J=7.5 Hz, 2H, ArH), 7.53 (d, J=7.5 Hz, 2H, ArH), 7.3–7.5 (m, 4H, ArH), 7.27 (br s, 2H, NH), 7.0–7.2 (m, 4H, ArH), 6.90 (br s, 2H, NH), 6.74 (t, J=7.5 Hz, 2H, ArH), 4.63 (m, 2H, CH-cycl), 4.40 (s, 4H, $CH_2CO$), 2.37 (m, 2H, CH-cycl), 1.7–1.9 (m, 6H, CH-cycl). IR (KBr) data: 1662 (CO), 1615 (C=N), 895 (O-U-O). Mass spectrum (FAB): m/z 889.4 (calculated 889.3). Element analysis: calculated for $C_{36}H_{34}N_4O_8U$ 1.18 $H_2O$: C=47.40; H=4.00; N=6.16. Found: C=46.99; H=4.15; N=5.77.

Karl Fischer titration: calculated for 1.18 H20: 2.34. Found: 2.34.

Example 5

Ionophore 10

A mixture of bromoacetamide (10 mM), 3-hydroxy-2-(2-propenoxy)-benzaldehyde (20 mM) and $K_2CO_3$ (40 mM) in $CH_3CN$ (200 ml) was refluxed for 10–12 hours. The solution was filtered and a solvent was evaporated. The remaining solid was purified by flash chromatography ($SiO_2$; $CH_2Cl_2$-acetone, 1:1). The yield amounted to 79%, melting point 98°–102° C.

$^1$H NMR data: δ10.46 (s, 2H, CHO), 7.50 (d, J=8.0 Hz, 2H, ArH), 7.0–7.2 (m, 6H, ArH +NH), 6.10 (m, 2H, $OCH_2CHCH_2$), 5.40 (m, 4H, $OCH_2CHCH_2$), 4.61 (d, J=6.0 Hz, 4H, $OCH_2CHCH_2$), 4.53 (s, 4 H, $CH_2CO$ ), 3.5–3.7 (m, 12 H, $CCH_2$ ). IR (KBr) data: 1693 (CO), 1653 (CHO). Mass spectrum (FAB): m/z 585.3 (calculated 585.2 ). Element analysis: calculated for $C_{30}H_{36}N_2O_{10}$: C=61.64; H=6.17; N=4.79. Found: C=61.66; H=6.37; N=4.87.

A mixture of the obtained allyl compound (5 mM), $Pd(OAc)_2$ (0.1 mM), $PPh_3$, (0.5 mM), $NEt_3$ (37 mM) and HCOOH (37 mM) in 80% aqueous ethanol (60 ml) was refluxed for 45 minutes. Ethanol was evaporated and the total water volume was adjusted to 100 ml. The mixture was extracted with $CH_2Cl_2$. The organic layer was dried over $Na_2SO_4$ and concentrated under vacuum. The yield amounted to 65%.

$^1$H NMR data: δ11.10 (br s, 2H, OH), 9.90 (s, 2H, CHO), 7.45 (br s, 2H, NH), 7.22 (d, J=8.0 Hz, 2H, ArH), 7.09 (d, J=8.0 Hz, 2H, ArH), 6.93 (t, J=8.0 Hz, 2H, ArH), 4.52 (s, 4H, $CH_2C(O)$), 3.5–3.7 (m, 12H, $OCH_2$). IR (KBr) data: 1672 (CO), 1654 (CHO). Mass spectrum (FAB): m/z 505.9 (calculated 505.2).

The formed aldehyde (10 mmol in 30 mL MeOH) and, separately, 1,2-cis-cyclohexanediamine (10 mmol in 30 mL MeOH) was added under reflux to a solution of $Ba(OTf)_2$ (20 mmol) in MeOH (200 mL) for 30 minutes.

11 mmol thereof in 10 mL MeOH was added after 30 minutes and the reflux conditions were maintained for a further 30 minutes. Each reaction mixture was evaporated dry under vacuum and washed with a large quantity of water. Recrystallization from methanol provided the pure ionophore 10 with a yield of 59%, melting point 240°–241° C.

$^1$H NMR data: δ9.50 (s, 2H, CH=N), 8,68 (br s, 2H, NH), 7.41 (two d, J=7.9 Hz, 4H, ArH), 6.69 (t, J=7.9 Hz, 2H, ArH), 4.72 (d, J=4.4 Hz, 4H, $CH_2C(O)$), 4.50 (m, 2H, CH-cycl), 3.4–3.6 (m, 12H, $(OCH_2)$), 2.2 (m, 2H, CH-cycl), 1.6–1.9 (m, 6H, CH-cycl). IR (KBr) data: 1671 (CO), 1617 (C=N), 901 (O-U-O). Mass spectrum (FAB): m/z 851.5 (calculated 851.0). Element analysis: calculated for $C_{30}H_{36}N_4O_{10}U$ 1.8 $H_2O$: C=40.79; H=4.48; N=6.34. Found: C=41.16; H=4.49; N=5.92. Karl Fischer titration: calculated for 1.8 $H_2O$: 3.67. Found: 3.70.

Example 6

Ionophore 11

A mixture of 1-tosyl-2-(2-amidocarboxyl)-ethyleneglycol (0.89 g, 5 mmol), 3-hydroxy-2-(2-propenoxy)-benzaldehyde (1.67 g, 5 mmol) and $K_2CO_3$ (1.38 g, 10 mmol) in $CH_3CN$ (200 mL) was refluxed for 10–12 hours. The solution was filtered and the solvent was evaporated. The remaining solid was purified by recrystallization from 2-propanol. The yield amounted to 81% melting point 137 ° C.

$^1$H NMR data: (CDCL$_3$) $\delta$10.40 (s, CHO), 8.30 (d, J=8.0 Hz, 1H, ArH), 7.91 (br s, 1H, NH), 6.9–7.5 (m, 7H, ArH), 6.0–6.2 (m, 1H, OCH$_2$CHCH$_2$), 6.0 (br s, 1H, NH), 5.3–5.5 (m, 2H, OCH$_2$CHCH$_2$), 4.66 (d, 2H, OCH$_2$CHCH$_2$), 4.4–4.6 (m, 4H, OCH$_2$). IR (KBr) data: 1686 (CHO) cm$^{-1}$. Mass spectrum (FAB): m/z 342 2 ((M+H)$^+$, calculated 341.1).

The prepared compound was converted in accordance with example 1 into the aldehyde yield 62%, melting point 172°–174° C. (ethanol-PE).

$^1$NMR data(DMSO-d$_6$): $\delta$10.25 (s, 1H, CHO), 6.8–7.9 (m, 9H, ArH, NH), 4.3–4.6 (m, 4H, OCH$_2$). IR (KBr) data: 1663 (CHO) cm$^{-1}$. Mass spectrum (FAB): m/z 301.7 ((M+H)$^+$, calculated 301.1). Element analysis: calculated for C$_{16}$H$_{15}$O$_5$N 0.5 H$_2$O: C, 61.85; H, 5.15; N, 4.51. Found: C=61.73; H=4.92; N=4.40. Karl Fischer titration: calculated for 0.5 H$_2$O: 3.00. Found: 2.84.

The prepared aldehyde solution (0.3 g, 1 mmol ) and 1,2-cis-cyclohexanediamine (0.06 g, 0.5 mmol) in MeOH (100 ml) was refluxed for 1 hour. A solution of UO$_2$(OAc)$_2$2H$_2$O (0.21 g, 0.5 mmol) in MeOH (10 ml) was then added and the reaction mixture refluxed for 1 hour. The reaction mixture was cooled to room temperature. The formed precipitation was filtered and washed with MeOH. The yield amounted to 51%, melting point 200°–202° C. (methanol).

$^1$NMR data(DMSO-d$_6$): $\delta$9.46 (s, 2H, CH=N), 6.5–7.9 (m, 18H, ArH, NH), 4.4–4.8 (m, 10H, OCH$_2$, CH-cycl), 2.45 (m, 2H, CH-cycl), 1.7–2.0 (m, 6H, CH-cycl). IR (KBr) data: 1685 (CO), 1617 (C=N), 904 (O-U-O). Mass Spectrum (FAB): m/z 947.0 ((M+H)$^+$, calculated 948.3). Element analysis: calculated for C$_{38}$H$_{38}$O$_{10}$N$_4$U 2.2 H$_2$O: C, 46.16; H, 4.29; N, 5.67. Found: C=45.86; H=4.00; N=5.52. Karl Fischer titration: calculated for 2.2 H$_2$O: 4.00. Found 3.84.

Ionophore 5 is described in J. Org. Chem., 56, p. 2371-2380, (1991).

Ionophore 12 is known from J. Am. Chem. Soc, 110, p. 4994-5008, (1988).

We claim:

1. A membrane that is selective for anions comprising a membrane matrix said membrane matrix having bonded thereto an ionophore based on a uranyl complex with the general formula

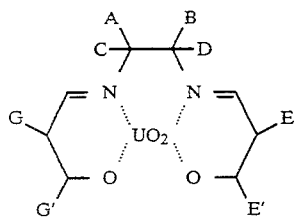

wherein A or B or C or D=R;
A and B and C and D is selected from the group consisting of (C$_5$-C$_7$) aryl
(C$_5$-C$_7$) cycloalkyl
(C$_1$-C$_{30}$) alkyl (C$_5$-C$_{10}$) aryl and
(C$_1$-C$_{30}$) alkyl (C$_5$-C$_{10}$) cycloalkyl;
wherein each of E +E' and G +G' is selected from the group consisting of aryl, aryl substituted with a substituent (C$_1$-C$_{30}$) alkoxy, and
aryl substituted with an individual substituent or the substituent joined by ring closure including
K and
K—CONH—L, wherein
K and L are selected from the group consisting of H
—R—(CH$_2$)$_m$—,   —R—(CH$_2$)$_m$—R,   —X—(CH$_2$)$_m$—, —X(CH$_2$)$_m$—R, —X—(CH$_2$)$_m$—X, —X(CH$_2$)$_m$—X—R,   —RX(CH$_2$)$_m$—,   —RX(CH$_2$)$_m$—XR and —X—(R—X)$_n$—, wherein
X=O, S
m=0–10 and
n=0–10; and
wherein R is selected from the group consisting of
(C$_1$-C$_{30}$) alkyl
(C$_5$-C$_{10}$) aryl
(C$_5$-C$_{10}$) cycloalkyl
(C$_1$-C$_{30}$) alkyl (C$_5$-C$_{10}$) aryl and
(C$_1$-C$_{30}$) alkyl (C$_5$-C$_{10}$) cycloalkyl,
wherein alkyl is a straight or branched chain substituted with the substituent Z$_Q$ wherein Z is selected from the group consisting of
(C$_1$-C$_{30}$) alkyl; a halogen atom; a nitro group; a cyano group; and a hydroxy group, and Q is 0–10, and
wherein aryl is substituted with a substituent T$_Y$
where T is selected from the group consisting of
(C$_1$-C$_{30}$) alkyl; a halogen atom; a nitro group; a cyano group; and a hydroxy group, wherein Y is 0–10.

2. Membrane as claimed in claim 1, wherein at least one of the substituent E+E' and the substituent G+G' is aryl substituted with the group K—CONH—L.

3. Membrane as claimed in claim 2, wherein the group K—CONH—L is the group X—(CH$_2$)$_m$—CONH—L.

4. Membrane as claimed in claim 3, wherein the substituent L is R.

5. Membrane as claimed in claim 4, wherein R is aryl.

6. Membrane as claimed in claim 5, with the structure formula for the ionophore of

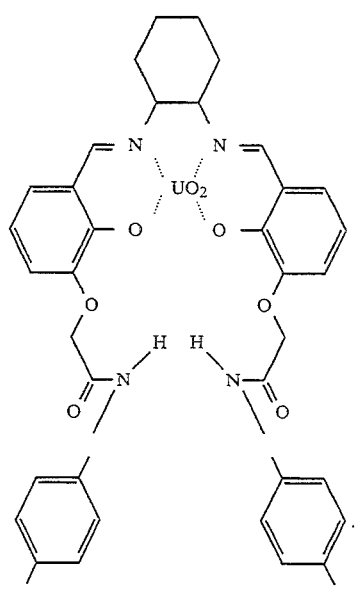

7. Membrane as claimed in claim 3, wherein the substituent L is H.

8. Membrane as claimed in claim 7, with the structure formula for the ionophore of

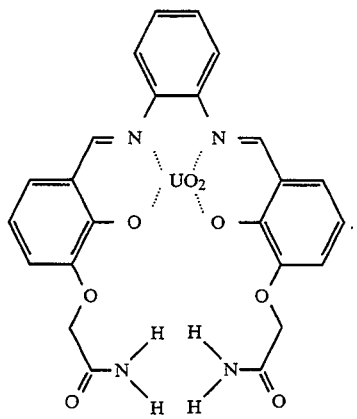

9. Membrane as claimed in claim 3, wherein the aryl substituent of the substituents E+E' and F+F' is a joint substituent K—COHN—L—NHCO—K formed by ring closure.

10. Membrane as claimed in claim 9, wherein the group L is $(CH_2)_m$—X—$(CH_2)_m$—X—$(CH_2)_m$.

11. Membrane as claimed in claim 10, wherein m=2 and X =O.

12. Membrane as claimed in claim 11, with the structure formula for the ionophore of

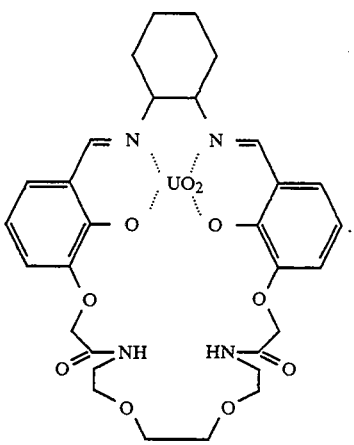

13. Membrane as claimed in claim 1, wherein at least one of the substituent E+E' and the substituent G+G' is —X—$(CH_2)_m$H.

14. Membrane as claimed in claim 13, wherein X=O.

15. Membrane as claimed in claim 14, with the structure formula for the ionophore of

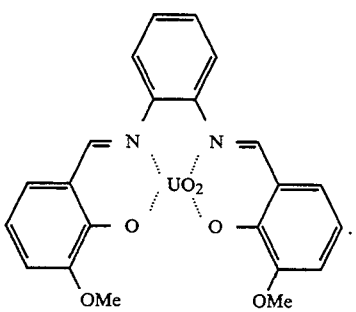

16. Membrane as claimed in claim 1, wherein the uranyl complex is provided with a group for linking to the membrane matrix.

17. Sensor provided with a membrane as claimed in claim 1.

* * * * *

UNITED STATES PATENT AND TRADEMARK OFFICE
CERTIFICATE OF CORRECTION

PATENT NO. : 5,380,423  Page 1 of 3
DATED : January 10, 1995
INVENTOR(S) : David N. Reinhoudt et al.

It is certified that error appears in the above-indentified patent and that said Letters Patent is hereby corrected as shown below: On the title page:

Abstract Line 24 "alkyl halogen nitro cyano hydroxy." should read --alkyl, halogen, nitro, cyano, hydroxy.--.

Column 1 Line 21 after "NL-A-8400916" insert --,--.

Column 1 Line 68 "alkyl halogen nitro cyano hydroxy;" should read --alkyl, halogen, nitro, cyano, hydroxy;--.

Column 2 Line 2 "alkyl halogen nitro cyano hydroxy." should read --alkyl, halogen, nitro, cyano, hydroxy.--.

Column 4, in the table, across from $Cl^-$, under 12 a, "nb" should read --nd--.

Column 5 Line 22 "$^1$NMR" should read --$^1$H NMR--.

Column 5 Line 28 "$C_9H_9NO_4H_2O$:" should read --$C_9H_9NO_4 \cdot H_2O$:--.

Column 5 Line 34 "$UO_2(OAc)_2H_2O$" should read --$UO_2(OAc)_2 2H_2O$--.

Column 5 Lines 40-41 "(m, 2H ArH)," should read --(m, 2H, ArH),--.

Column 6 Line 28 "8.87 (s" should read --8.87 (s,--.

UNITED STATES PATENT AND TRADEMARK OFFICE
CERTIFICATE OF CORRECTION

PATENT NO. : 5,380,423

DATED : January 10, 1995

INVENTOR(S) : David N. Reinhoudt et al.

It is certified that error appears in the above-indentified patent and that said Letters Patent is hereby corrected as shown below:

Column 6 Line 51 "CH])," should read --$CH_3$),--.

Column 7 Lines 2-3 "C=48,65; H=3,74; N=5,97," should read --C=48.65; H=3.74; N=5.97.--.

Column 7 Line 3 "H=3,57;" should read --H=3.57;--.

Column 7 Line 22 "1H ArH), 7.61" should read --1H, ArH), 7.61--.

Column 7 Line 48 "$CH_2$CO." should read --$CH_2$CO).--.

Column 8 Line 1 "H2O:" should read --$H_2O$:--.

Column 8 Line 49 "8,68" should read --8.68--.

Column 9 Line 9 "342 2" should read --342.2--.

Column 9 Line 12 after "aldehyde" insert --,--.

Column 9 Line 14 "$^1$NMR" should read --$^1$H NMR--.

UNITED STATES PATENT AND TRADEMARK OFFICE
CERTIFICATE OF CORRECTION

PATENT NO. : 5,380,423
DATED : January 10, 1995
INVENTOR(S) : David N. Reinhoudt et al.

It is certified that error appears in the above-indentified patent and that said Letters Patent is hereby corrected as shown below:

Column 9 Line 31 "$^1$NMR" should read --$^1$H NMR--.

Claim 1 Line 46 Column 9 "matrix said" should read --matrix, said--.

Signed and Sealed this

Twenty-fifth Day of April, 1995

Attest:

BRUCE LEHMAN

*Attesting Officer*    *Commissioner of Patents and Trademarks*